(12) United States Patent
Hempel

(10) Patent No.: US 8,027,428 B2
(45) Date of Patent: Sep. 27, 2011

(54) CT SYSTEM AND METHOD FOR PHASE-CONTRAST AND ABSORPTION IMAGING

(75) Inventor: Eckhard Hempel, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/769,212

(22) Filed: Apr. 28, 2010

(65) Prior Publication Data

US 2010/0278298 A1 Nov. 4, 2010

(30) Foreign Application Priority Data

Apr. 30, 2009 (DE) .......................... 10 2009 019 514

(51) Int. Cl.
*A61B 6/00* (2006.01)
(52) U.S. Cl. ................................ 378/9; 378/4
(58) Field of Classification Search .................. 378/4, 9
See application file for complete search history.

(56) References Cited

U.S. PATENT DOCUMENTS

| | | | |
|---|---|---|---|
| 4,204,124 A * | 5/1980 | Kowalski | 378/9 |
| 6,885,442 B1 | 4/2005 | Nugent et al. | |
| 7,197,106 B2 * | 3/2007 | Hartung et al. | 378/19 |
| 7,412,024 B1 | 8/2008 | Wang et al. | |
| 7,412,026 B2 | 8/2008 | Liu | |
| 7,421,062 B2 * | 9/2008 | Okumura et al. | 378/116 |
| 2005/0062957 A1 | 3/2005 | Nugent et al. | |
| 2007/0153979 A1 | 7/2007 | Baumann et al. | |
| 2007/0183558 A1 * | 8/2007 | Hempel | 378/4 |
| 2008/0123803 A1 * | 5/2008 | De Man et al. | 378/9 |

FOREIGN PATENT DOCUMENTS

| | | |
|---|---|---|
| DE | 69924136 T2 | 4/2006 |
| DE | 102006015356 A1 | 8/2007 |
| JP | 54092192 A * | 7/1979 |
| JP | 2003325501 A | 11/2003 |
| WO | WO 0026622 A1 | 5/2000 |
| WO | WO 03/034010 | 4/2003 |

OTHER PUBLICATIONS

Quantitative Phase Imaging, Investment Research www.iatia.com.au/investors/researchCoverage/intersuisseResearch0408.pdf; Others; 2008.

(Continued)

*Primary Examiner* — Edward J Glick
*Assistant Examiner* — Alexander H Taningco
(74) *Attorney, Agent, or Firm* — Harness, Dickey & Pierce, P.L.C.

(57) ABSTRACT

A CT system is disclosed for phase-contrast and absorption imaging with a plurality of emitter-detector systems. In at least one embodiment, there are at least two emitter-detector systems and the at least two emitter-detector systems have a different distance between radiation focus and detector and there is a computational element for calculating phase-contrast images on the basis of the solution to the intensity transport equation. Moreover, at least one embodiment of the invention relates to a method for phase-contrast and absorption imaging using such a CT system by comparing attenuation images recorded at different distances of a detector from a multiplicity of projection angles by solving the intensity transport equation and reconstruction or comparison of two tomographic and three-dimensional image data records, reconstructed from projections, which were recorded at different distances.

13 Claims, 2 Drawing Sheets

OTHER PUBLICATIONS

Keith A. Nugent, "Astigmatic diffraction—A unique solution to the non-crystallographic phase problem", School of Physics, The University of Melbourne, Australia; Others; 1996.

Langer, Max et al., Quantitative comparison of direct phase retrieval algorithms in in-line phase tomography, Medical Physics 35 (2008) pp. 4556-4566; Others.

Zoofan, B. et al., Application of Phase Contrast Microradiography in NDT, Materials Evaluation 63 (2005) pp. 1122-1127; Others.

K.A. Nugent et al. "Quantitative Phase Imaging Using Hard X-Rays" Physical Review Letters, vol. 77, No. 14, Sep. 30, 1996, pp. 2961-2964.

* cited by examiner

CT SYSTEM AND METHOD FOR PHASE-CONTRAST AND ABSORPTION IMAGING

PRIORITY STATEMENT

The present application hereby claims priority under 35 U.S.C. §119 on German patent application number DE 10 2009 019 514.9 filed Apr. 30, 2009, the entire contents of which are hereby incorporated herein by reference.

FIELD

At least one embodiment of the invention generally relates to a CT system for phase-contrast and absorption imaging. In particular, at least one embodiment relates to a CT system with a gantry that can rotate about a system axis, with at least two emitter-detector systems, which are attached to the gantry with an angular offset and scan a measurement field, wherein there is a specified distance between a radiation focus in the emitter and the detector with its detector elements in each emitter-detector system and measurement beams are defined by the geometric connection between radiation focus and detector element, and with a computational and control unit for controlling the CT system.

Furthermore, at least one embodiment of the invention generally relates to a method for phase-contrast and absorption imaging with a dual-emitter- or multi-emitter-detector CT system. In particular, at least one embodiment relates to a method wherein a gantry, on which at least two emitter-detector systems are attached with an angular offset, rotates about a system axis and an examination object is scanned in a measurement field and at least two attenuation images are recorded for each projection angle at a multiplicity of projection angles.

BACKGROUND

CT systems for generating quantitative tomographic phase-contrast images with the aid of at least one phase grating in the beam path of the emitter-detector system, that is to say using interferometric measurement methods, are generally known. It is very demanding to produce the X-ray optical gratings required for this because they have to have structure geometries with a structure width of approximately 1 μm and a structure height of approximately 100 μm, corresponding to an aspect ratio of approximately 100. The use of said method in CT systems that can be used clinically is made more difficult as a result of this problem, which is difficult to solve technologically on a clinical scale.

SUMMARY

In at least one embodiment of the invention, a CT system and/or a CT method are capable of carrying out phase-contrast measurements, even without the use of phase gratings.

In at least one embodiment, the inventor has recognized that it is possible to transfer to a CT system a method known per se for determining phase shifts in a wave front, in which the wave front is measured at different distances and the intensity transport equation is solved. This affords the possibility of determining the phase shift within a wave front emanating from the focus of an X-ray beam source by recording each projection at least two different distances and determining the intensity derivatives thereof in the beam direction. The intensity transport equation can be solved on the basis of this data, preferably with the aid of multiple Fourier transforms and inverse transforms, and the phase shift per beam can be determined. The phase shifts per beam determined in this fashion, that is to say phase-shift projections from a multiplicity of projection directions, then allow the determination of tomographic illustrations of the examination object in respect of local refractive indices.

In principle, it is alternatively also possible to solve the intensity transport equation on the basis of projections, measured at different distances, and tomographic image data records reconstructed therefrom.

Thus, this algorithm allows the extraction of the phase information from incoherent, polychromatic radiation without the use of special optical components such as X-ray optical gratings. The algorithm determines the phase information from two conventional intensity measurements recorded in different focal planes.

In accordance with these findings, in at least one embodiment the inventor proposes to improve a CT system for phase-contrast and absorption imaging, with:
  a gantry that can rotate about a system axis,
  at least two emitter-detector systems, which are attached to the gantry with an angular offset and scan a measurement field, wherein:
    there is a specified distance between a radiation focus in the emitter and the detector with its detector elements in each emitter-detector system,
    measurement beams are defined by the geometric connection between radiation focus and detector element,
  and a computational and control unit for controlling the system,
to the effect that at least two of the emitter-detector systems have a different distance between radiation focus and detector.

The radiation foci of the at least two emitters should preferably have the same distance from the system axis. The effect of this is that the deflections generated in the beam path by different local refractive indices in an examination object, in particular a patient being examined, lead to intensity differences at different distances due to phase shifts, per beam, in the projection images, which intensity differences in end effect result in the basis for solving the intensity transport equation.

It is furthermore proposed, in at least one embodiment, to design and position the detector elements of the detectors such that the detectors are formed in a congruent fashion in the projection as seen from the foci. This means that both detectors have the same number and distribution of detector elements and so—without phase shifts by the examination object—this would have to result in congruent projection data. This significantly simplifies the differential equation because only pixel-by-pixel differences have to be determined in the projections.

The CT system according to at least one embodiment of the invention should furthermore have a computational unit, which:
  has a computational element for solving the transport intensity equation on the basis of at least two projections recorded at the same projection angle at different distances, which outputs phase and intensity values of the measurement beams for a multiplicity of projection angles, and
  has a computational element for reconstructing tomographic image data from the calculated phase values and/or intensity values.

In particular, the computational element for solving the transport intensity equation can have the following computational sub-elements:

a)—a differentiation element in the direction of the measurement beam;
b)—a multiplication element with an average weighted wavenumber of the X-ray spectrum used for the examination;
c)—a transform computational element for performing a transform into the spatial-frequency space;
d)—a splitter for splitting the transforms into two orthogonal directions, respectively in one computational branch;
e)—a first filter in each computational branch;
f)—a first inverse transform computational element in each computational branch for performing an inverse transform into the real space;
g)—a division element in each computational branch for dividing by the intensity values;
h)—a first transform computational element in each computational branch for performing a transform into the spatial-frequency space;
i)—a second filter in each computational branch;
j)—a second inverse transform computational element in each computational branch for performing an inverse transform into the real space;
k)—an adding element for adding the results per measurement beam in each computational branch; and
l)—an output computational element for the phase recovered per measurement beam.

Herein, the transform and inverse transform computational elements can be designed as FFT or $FFT^{-1}$ computational elements (FFT=fast Fourier transform, $FFT^{-1}$=inverse FFT).

As an alternative to the FFT computational elements, the transform and inverse transform computational elements can also be designed as wavelet or inverse wavelet computational elements.

In accordance with the basic idea of at least one embodiment of the invention, an improved method for phase-contrast and absorption imaging with a dual-emitter- or multi-emitter-detector CT system is also proposed, wherein a gantry, on which at least two emitter-detector systems are attached with an angular offset, rotates about a system axis and an examination object is scanned in a measurement field and at least two attenuation images are recorded for each projection angle at a multiplicity of projection angles. The improvement lies in the fact that the at least two attenuation images per projection angle recorded at different distances from the emitter are used to determine intensity gradients in the measurement beam direction, a phase value is calculated per measurement beam direction by solving the intensity transport equation, and a tomography image is calculated from the phase values from a multiplicity of projection angles.

The formula of the intensity transport equation is given by $$\nabla_\perp \cdot (I \Delta_\perp \phi) = -k \frac{\partial I}{\partial z},$$

where I is the measured radiation intensity and $\phi$ is the phase of the beam under consideration.

In at least one embodiment of the method, the following method steps can be carried out in order to solve the transport intensity equation:
a)—differentiating the measurement data of the same measurement beams in the measurement beam direction;
b)—multiplication element with an average weighted wavenumber of the X-ray spectrum used for the examination;
c)—transform into the spatial-frequency space;
d)—splitting the transforms into two orthogonal directions, respectively into a computational branch;
e)—applying a first filter in each computational branch;
f)—performing an inverse transform into the real space in each computational branch;
g)—dividing by the intensity values of the measurement beam in each computational branch;
h)—performing a transform into the spatial-frequency space in each computational branch;
i)—filtering using a second filter in each computational branch;
j)—performing an inverse transform into the real space in each computational branch;
k)—adding the results per measurement beam in each computational branch; and
l)—outputting the phase recovered per measurement beam.

On the one hand, the transform and inverse transform can in this case be carried out as a Fourier transform and inverse Fourier transform, and, on the other hand, the transform and inverse transform can also be carried out as wavelet and inverse wavelet computational elements.

BRIEF DESCRIPTION OF THE DRAWINGS

In the following text, the invention will be described in more detail on the basis of an example embodiment with the aid of the figures, with only the features required for the understanding of the invention being illustrated. Herein, the following reference signs are used: D1, D2: detectors; F1, F2: foci; R1, R2: distances between focus and detector; P: patient; SR: control and computational unit; S.01-S.21: method steps; N.1-N.4: coordinate method steps; $Prg_1$-$Prg_n$: computer programs.

In detail.

DETAILED DESCRIPTION OF THE EXAMPLE EMBODIMENTS

Figure 1:
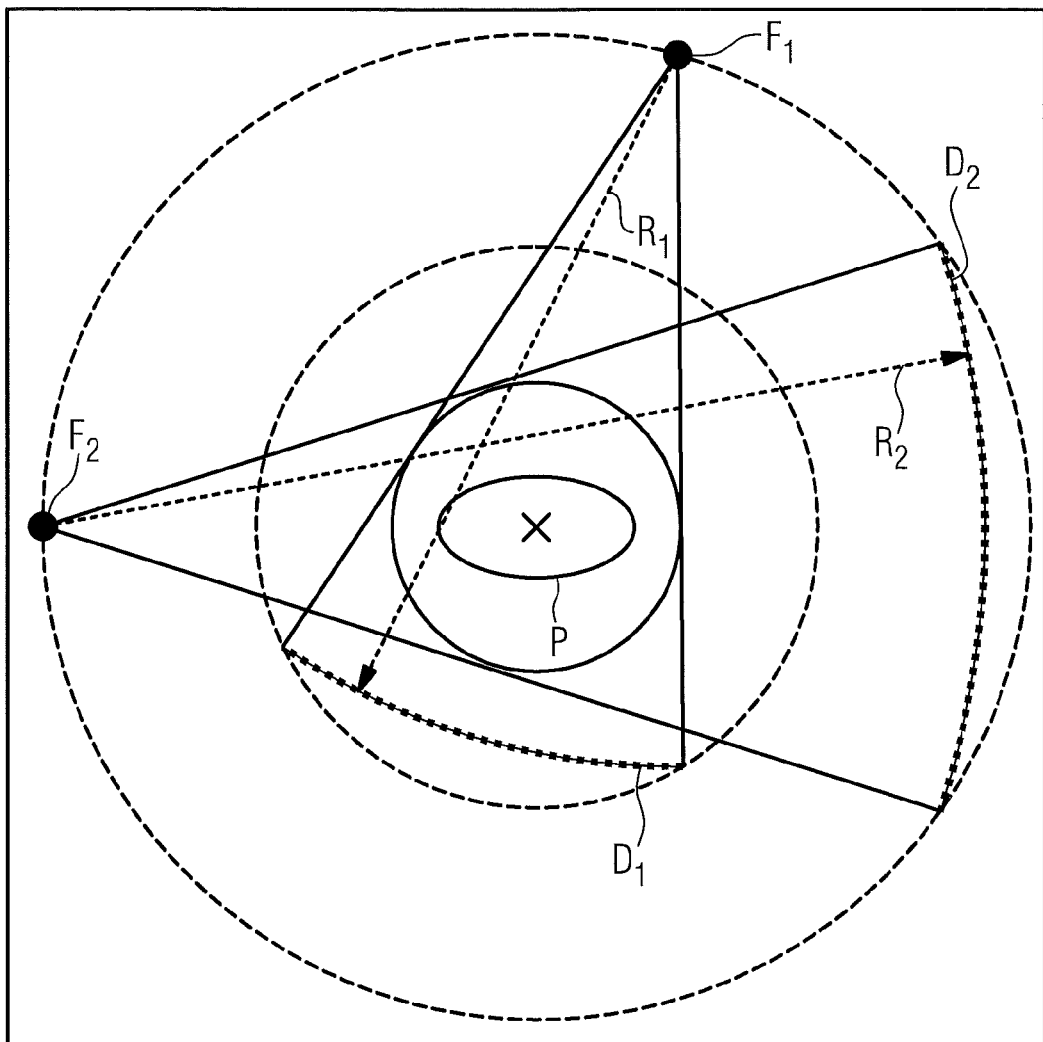
FIG. 1 shows a schematic illustration of a CT system with two emitter-detector systems and FIG. 2 shows a flowchart for solving the intensity transport equation on the basis of two projective attenuation measurements by a CT system.
Figure 1:
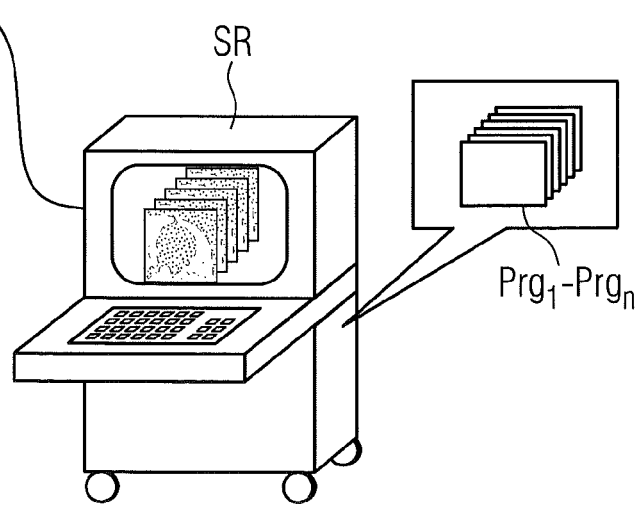

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic illustration of a CT system with two emitter-detector system arranged with an angular offset, respectively consisting of a focus F1 or F2 and an opposing detector D1 or D2. The detectors D1 and D2 are arranged at respectively different distances R1 and R2 from the associated focus and on an encircling gantry (not illustrated here). Due to the different distances of the detectors from the examination object P, this results in two projection recordings from two projections recorded at the same angular position, which projection recordings differ in their normalized intensity distribution only as a result of refractive-index-dependent deflection of the beams passing through the examination object. Thus, when imaging an ideal sphere, a relative smearing of the intensity occurs that exceeds the perspective enlargement resulting from the larger distance. This smearing is caused by a beam deflection due to different run-times, that is to say by a different phase shift when passing through the object.

It is generally known from the relevant literature that quantitative calculation of the phase shift per beam is possible on the basis of the intensity differences, occurring per beam, between two projections recorded at different distances and the solution of the intensity transport equation. Thus, a phase-contrast measurement can also be performed without using interferometric methods, in particular without using phase gratings arranged in the beam path. Knowledge of the quantitative phase-shift values per beam and reconstruction allows conclusions to be drawn in respect of the distribution of the refractive indices.

A control and computational unit SR is used to control the CT system and calculate the intensity transport equation, and it keeps ready computer programs $Prg_1$-$Prg_n$ in its storage for this purpose and executes said programs when necessary.

Figure 2:
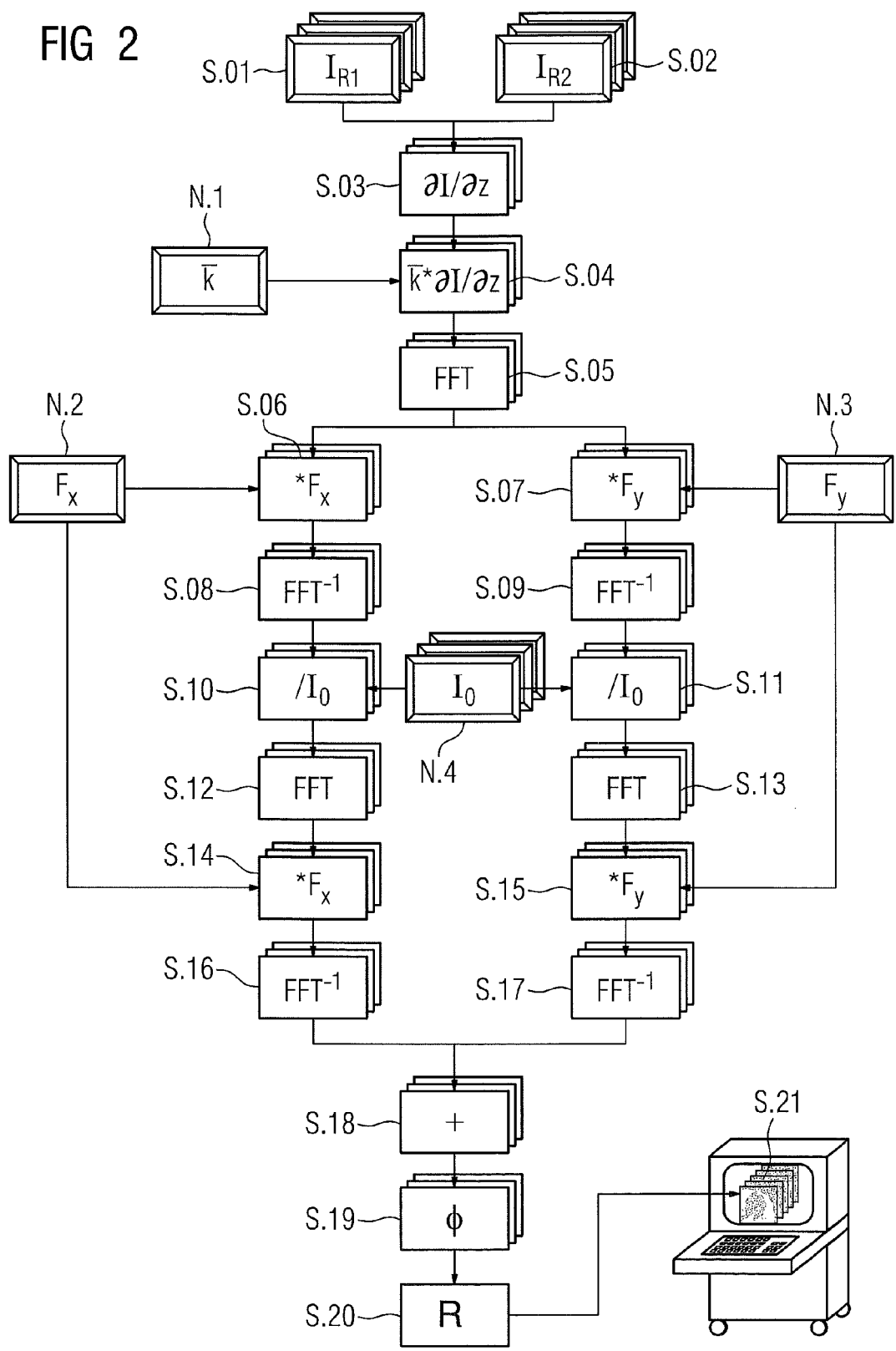

An example flowchart for solving the intensity transport equation on the basis of projective attenuation measurement of a CT system at different distances from the examination object is shown in FIG. 2.

In principle, the method is carried out for a multiplicity of projection angles. In the illustration, this is indicated by the multiply covered method schematics. The following description relates firstly to the treatment of the projection recordings of a projection angle.

In accordance with the illustrated flowchart, two projection recordings $I_{R1}$ and $I_{R2}$ are generated for each projection angle in steps S.01 and S.02 with the aid of the two emitter-detector system from FIG. 1. The two detector systems used for this are at different radial distances R1 and R2 from their associated radiation source, but said sources are at the same distance from the system axis of the CT system.

In the next step S.03, the spatial derivative $\partial I/\partial z$ of the intensities per beam in the beam direction z is calculated. In a coordinate calculation in step N.1, an average wavenumber $\bar{k}$ of the utilized radiation is calculated, the derivative $\partial I/\partial z$ determined previously in step S.03 being multiplied thereby. Subsequently, the two-dimensional data record obtained thus is transformed into spatial-frequency spaces with respect to two independent directions of the image plane (in this case in the x- and y-direction), preferably by means of a Fourier transform FFT. The data record obtained in this fashion is then split in respect of its directions and is treated separately in each case. In the illustrated method scheme, the calculation method now splits into the steps with an even or odd index, according to the spatial frequencies in the x- or y-direction.

In steps S.06 and S.07, the data records are multiplied by in each case one of filters $F_x$ and $F_y$ in parallel, which filters were calculated previously in coordinate steps N.2 and N.3, and this is followed by a subsequent inverse transform $FFT^{-1}$ in step S.08 or 5.09. The filters $F_x$ and $F_y$ described here are designed such that they correspond to an inversion of a differential operator reflected in the transformed representation of the spatial-frequency space. If necessary, correction elements can also be included in these filters, which correction elements correct possibly occurring imaging errors in the utilized imaging system, i.e. the emitter-detector combination.

In steps S.10 and S.11, the data records determined to this point in the two method branches are optionally divided by an average intensity $I_0$ determined in a coordinate step N.4. The average intensity results from averaging the intensity measurements at the two distances R1 and R2, wherein this normalization is carried out if the average intensity exceeds a predetermined value.

Subsequently, there is another Fourier transform in steps S.12 and S.13, and this is followed by another filtering using the filters $F_x$ and $F_y$ in steps S.14 and S.15, with another inverse transform $FFT^{-1}$ in steps S.16 and S.17. The data records produced in the two method branches are added in step S.18 and, as a result, the phases $\phi$ thus determined per beam are output in step S.19 for each projection angle. Using these results from a multiplicity of projection angles, it is now possible in step S.20 to carry out a reconstruction using reconstruction algorithms known per se.

In step S.21, at least the determined volume-specific phases of the X-ray radiation are output. Alternatively, a volume-specific refractive index can also be calculated from the determined phases and said refractive index can be output. Additionally, the output image display can also show a parallel display or a superposition of a conventional CT attenuation image on the phase-contrast image obtained in this fashion.

In respect of the method described briefly above and relating to the solution of the intensity transport equation by differentiation, filtering and multiple transforms and inverse transforms into the spatial-frequency space, reference is additionally made to the document WO 00/26622, the entire contents of which are hereby incorporated herein by reference.

Thus, overall, an embodiment of the invention describes a CT system for phase-contrast and absorption imaging with a plurality of emitter-detector systems, wherein there are at least two emitter-detector systems and the at least two emitter-detector systems have a different distance between radiation focus and detector and there is a computational element for calculating phase-contrast images on the basis of the solution to the intensity transport equation. Moreover, an embodiment of the invention also describes a method for phase-contrast and absorption imaging using such a CT system by comparing attenuation images recorded at a different distance of a detector from a multiplicity of projection angles by solving the intensity transport equation and reconstruction or comparison of two tomographic and three-dimensional image data records, reconstructed from projections, which were recorded at different distances.

It is understood that the aforementioned features of the invention can be used not only in the respectively specified combination, but also in other combinations or on their own, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A CT system for phase-contrast and absorption imaging, comprising:
   a gantry, rotatable about a system axis;
   at least two emitter-detector systems, attached to the gantry with an angular offset to scan a measurement field, a specified distance existing between a radiation focus in a respective emitter and a respective detector with its detector elements in each of the at least two emitter-detector systems, measurement beams being defined by a geometric connection between respective a radiation focus and detector element, and at least two of the at least two emitter-detector systems including different distances between respective radiation focus and detectors; and
   a computational and control unit configured to control the CT system, the computational and control unit including a computational element configured to solve a transport intensity equation on the basis of at least two projections recorded at the same projection angle at different distances, which outputs phase and intensity values of the measurement beams for a multiplicity of projection angles, and including a computational element configured to reconstruct tomographic image data from at least one of the calculated phase values and intensity values.

2. The CT system as claimed in claim 1, wherein the radiation foci of the at least two emitters have the same distance from the system axis.

3. The CT system as claimed in claim 1, wherein the detector elements of the detectors are positioned such that the detectors are formed in a congruent fashion in the projections as seen from the foci.

4. The CT system as claimed in claim 1, wherein the detector elements of the detectors are designed and positioned such that the detectors are formed in a congruent fashion in the projections as seen from the foci.

5. The CT system as claimed in claim 1, wherein the computational element for solving the transport intensity equation has the following computational sub-elements:
   a differentiation element in a direction of the measurement beam;
   a multiplication element with an average weighted wavenumber of the X-ray spectrum used for the examination;
   a transform computational element configured to perform a transform into spatial-frequency space;
   a splitter for splitting the transforms into two orthogonal directions, respectively in one computational branch;
   a first filter in each computational branch;
   a first inverse transform computational element in each computational branch configured to perform an inverse transform into real space;
   a division element in each computational branch configured to divide by the intensity values;
   a first transform computational element in each computational branch configured to perform a transform into spatial-frequency space;
   a second filter in each computational branch;
   a second inverse transform computational element in each computational branch for performing an inverse transform into real space;
   an adding element configured to add the results per measurement beam in each computational branch; and
   an output computational element for the phase recovered per measurement beam.

6. The CT system as claimed in claim 5, wherein the transform and inverse transform computational elements are Fast Fourier Transform (FFT) or Inverse Fast Fourier Transform ($FFT^{-1}$) computational elements.

7. The CT system as claimed in claim 5, wherein the transform and inverse transform computational elements are wavelet or inverse wavelet computational elements.

8. The CT system as claimed in claim 1, further comprising a computational and control unit for controlling the CT system.

9. A method for phase-contrast and absorption imaging with a dual-emitter- or multi-emitter-detector CT system, wherein a gantry, on which at least two emitter-detector systems are attached with an angular offset, is configured to rotate about a system axis to scan an examination object in a measurement field and at least two attenuation images are recorded for each projection angle at a multiplicity of projection angles, the method comprising:
   using the at least two attenuation images per projection angle, recorded at different distances from the emitter, to determine intensity gradients in a measurement beam direction;
   calculating a phase value per measurement beam by solving a transport intensity equation; and
   calculating a tomography image from the calculated phase values from a multiplicity of projection angles.

10. The method as claimed in claim 9, comprising the following to solve the transport intensity equation:
    differentiating the measurement data of the same measurement beams in the measurement beam direction;
    using a multiplication element with an average weighted wavenumber of the X-ray spectrum for the examination;
    transforming into spatial-frequency space;
    splitting the transforms into two orthogonal directions, respectively into a computational branch;
    applying a first filter in each computational branch;
    performing an inverse transform into real space in each computational branch;
    dividing by the intensity values of the measurement beam in each computational branch;
    performing a transform into spatial-frequency space in each computational branch;
    filtering using a second filter in each computational branch;
    performing an inverse transform into real space in each computational branch;
    adding the results per measurement beam in each computational branch; and
    outputting the phase recovered per measurement beam.

11. The method as claimed in claim 10, wherein the transform and inverse transform are carried out as a Fourier transform and inverse Fourier transform.

12. The method as claimed in claim 10, wherein the transform and inverse transform are wavelet and inverse wavelet computational elements.

13. A non-transitory computer readable medium including program segments for, when executed on a computer device, causing the computer device to implement the method of claim 9.

* * * * *